United States Patent [19]

Hull

[11] 4,133,833
[45] Jan. 9, 1979

[54] PRODUCTION OF N,N-DI(ETHYL)-META-TOLUAMIDE FROM META-TOLUIC ACID BY LIQUID PHASE CATALYTIC REACTION WITH DIETHYLAMINE

[75] Inventor: Ezekiel H. Hull, Greensboro, N.C.

[73] Assignee: Pfizer Inc., New York, N.Y.

[21] Appl. No.: 868,120

[22] Filed: Jan. 9, 1978

[51] Int. Cl.² .................. C07C 103/22; C07C 103/76
[52] U.S. Cl. ............................ 260/558 R; 252/431 R
[58] Field of Search ................ 260/558 R; 252/431 R

[56] References Cited

U.S. PATENT DOCUMENTS

| | | | |
|---|---|---|---|
| 2,932,665 | 4/1960 | Wagner | 260/558 R |
| 3,198,831 | 8/1965 | Stryk | 260/558 R |
| 3,825,596 | 7/1974 | Naito et al. | 260/558 R |
| 3,833,677 | 9/1974 | Grard | 260/558 R |
| 4,054,576 | 10/1977 | Baker et al. | 260/558 R |

*Primary Examiner*—Allen B. Curtis
*Assistant Examiner*—Raymond Covington
*Attorney, Agent, or Firm*—Connolly and Hutz

[57] ABSTRACT

Meta-toluic acid reacts with diethylamine in the liquid phase at elevated temperatures in the presence of a catalyst selected from the group consisting of titanium tetrachloride and certain organic titanates to form N,N-diethyl-meta-toluamide.

8 Claims, No Drawings

PRODUCTION OF N,N-DI(ETHYL)-META-TOLUAMIDE FROM META-TOLUIC ACID BY LIQUID PHASE CATALYTIC REACTION WITH DIETHYLAMINE

BACKGROUND OF THE INVENTION

N,N-di(n-lower alkyl)-meta-toluamides are useful as agricultural agents and insecticides. In particular, N,N-diethyl-meta-toluamide is widely used as an active ingredient in insect repellent formulations. Because of its availability and relatively low cost, meta-toluic acid is a highly preferred starting material in the preparation of these compounds. Thus, one known method of preparing N,N-diethyl-m-toluamide is a two-step process in which m-toluic acid and phosphorus oxychloride are reacted in the liquid phase with diethylamine. One disadvantage of this known method is the cost of phosphorus oxychloride and alkali needed to neutralize residual amounts of this reactant after completion of the first step. Another disadvantage is the generation of gaseous hydrogen chloride as a reaction product in the second step of the preparation.

U.S. Pat. Nos. 2,932,665 and 3,198,831 disclose processes for the preparation of N,N-diethyl-toluamides involving the reaction of a toluic acid with diethylamine in the vapor phase in the presence of silica gel, alumina or boron phosphate catalyst. The former of these patents also teaches that liquid phase reaction of m-toluic acid with diethylamine in the presence or absence of a dehydration catalyst to produce N,N-diethyl-m-toluamide is marked by long reaction times plus generation of objectionable amounts of odor and color bodies and undesired by-products, and that the catalyzed and uncatalyzed reaction yields are substantially the same.

U.S. Pat. No. 3,825,596 discloses a liquid phase process for producing N,N-di(lower alkyl)-m(and p)-toluamides in which m(or p)-tolunitrile, a di(lower alkyl) amine and water are contacted at a temperature of 100° C. to 400° C., preferably in the presence of a catalyst selected from the group consisting of inorganic acids, organic acids, organic acid metal salts, metal halides, and peroxides. The preferred organic acid metal salts and metal halides are the acetates and chlorides of copper, zinc, cadmium, mercury, nickel, cobalt and lead. Care must be taken to remove ammonia, a reaction product, from the reaction system in order to obtain a satisfactory reaction yield. U.S. Pat. No. 3,825,596 teaches that the process described therein is not a dehydration reaction.

SUMMARY OF THE INVENTION

It has now been discovered that the compound N,N-diethyl-meta-toluamide is prepared by a novel single-step process in which meta-toluic acid is contacted with diethylamine in the liquid phase at a temperature of about 150° C. to 300° C. in the presence of a catalyst in the amount of about 0.0001 to 0.1 gram per gram of said meta-toluic acid, said catalyst being selected from the group consisting of titanium tetrachloride, certain tetraalkyl titanates and certain organic titanate chelates, and the water produced by said preparation being removed from said liquid phase during the course of said preparation. The preferred temperature range is 205° C. to 250° C. The product N,N-di(ethyl)-meta-toluamide may be easily recovered from the reaction mixture by distillation.

DETAILED DESCRIPTION OF THE INVENTION

The process of the invention described herein follows the reaction formula

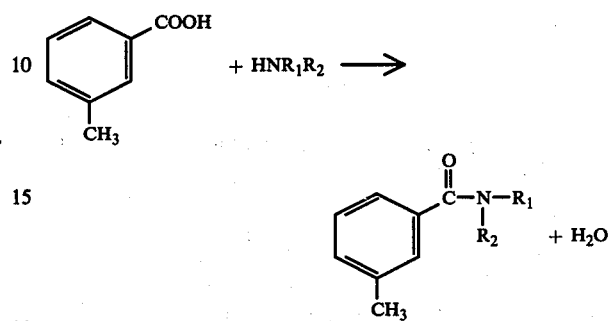

wherein $R_1$ and $R_2$ are both ethyl. The two reactants, meta-toluic acid and diethylamine, are mutually soluble in the liquid state at temperatures above 110° C., the melting point of m-toluic acid. Although the broad conception of this invention includes operation in the presence of a reaction-inert solvent, it is not necessary to introduce such a solvent in order to maintain a homogeneous liquid phase. As will be discussed below a small quantity of solvent may be added to the reaction mixture for an unrelated purpose, i.e., to serve as an azeotroping agent for convenient removal of water produced by the reaction. Other than this, however, it is preferred to perform the process in the absence of any reaction-inert solvent in order to maximize the productivity per unit of reaction volume.

The novel liquid phase reaction of m-toluic acid with diethylamine is catalyzed by a catalyst present in the reaction mixture in an amount of from about 0.0001 to about 0.1 gram per gram of m-toluic acid introduced. The preferred catalyst level is an amount of from about 0.001 to about 0.02 gram per gram of m-toluic acid introduced. The catalyst is selected from the group consisting of (a) titanium tetrachloride;

(b) $Ti(OA)_4$ wherein the four A moieties may be identical or not and each is selected from the group consisting of alkyl of from 3 to 18 carbon atoms, such as n-propyl, n-butyl, n-pentyl, n-hexyl, n-heptyl, n-octyl, n-nonyl, isopropyl and 2-ethylhexyl;

(c) a triethanolamine titanate chelate such as the one of the formula

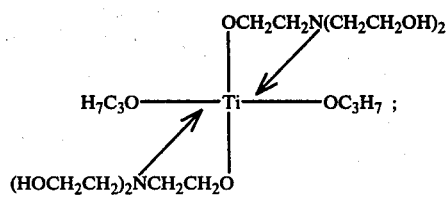

(d) a titanium acetylacetonate chelate such as the one of the formula

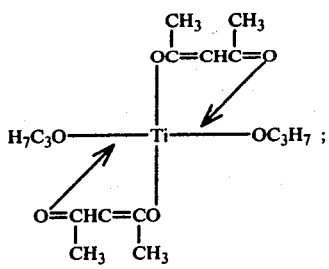

(e) a tetraoctylene glycol titanate chelate such as the one of the formula

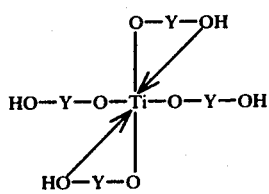

wherein Y is $$-CH_2CHCH- ;$$
with substituents $C_2H_5$ and $C_3H_7$

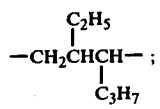

(f) and a titanium lactate ammonium salt chelate such as the one of the formula

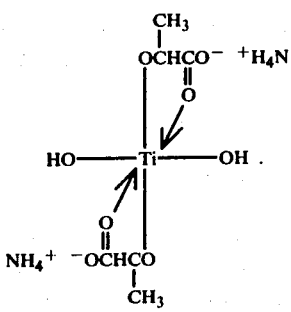

Catalyst (a) is a well-known commercial product. The specific catalysts whose formulae are given under (c) to (f) above and some of those among the definition of (b) are commercially available under the name of Tyzor (E. I. du Pont de Nemours and Co., Inc., Wilmington, Del.) catalysts. Catalyst groups (c) to (f) are described in U.S. Pat. No. 2,824,114; British Pat. No. 734,113; and U.S. Pat. Nos. 2,643,262 and 2,870,181, respectively. Catalyst (a) and those of (b) above are liquids at temperatures above about 60° C. Many are liquids at room temperature. The specific catalysts whose formulae are given under (c) to (f) above are commercially available in the following forms:

| Catalyst | Commercially Available Form | Name of Commercially Available Form |
|---|---|---|
| (c) | 80% solution in isopropanol | Tyzor TE |
| (d) | 75% solution of isopropanol | Tyzor AA |
| (e) | 100% (liquid at room temperature) | Tyzor OG |

-continued

| Catalyst | Commercially Available Form | Name of Commercially Available Form |
|---|---|---|
| (f) | 50% solution in Water | Tyzor LA |

The active chelate ingredient in each of these commercially available forms of catalysts (c) to (f) exists in a partially polymerized state (via intermolecular alcoholysis). One preferred group of catalysts consists of the catalysts of (b) above. Another preferred group consists of tetra(n-butyl) titanate of (b) above and the triethanolamine titanate chelate catalysts of (c) above. The specific triethanolamine titanate chelate whose formulae is given in (c) above (commercially available as Tyzor TE) is the most preferred catalyst because of its relatively low cost, and the high conversions and yields and low corrosion rates of stainless steel 316, a commonly used material of construction for reaction vessels, obtained with its use. Titanium tetrachloride is not a preferred catalyst because of handling problems and excessive corrosion of stainless steel 316 associated with its use, but it may be employed, e.g. in glass-lined equipment.

The novel process of this invention is conducted at a temperature of about 150° C. to 300° C. Utilization of temperatures below this range results in reaction rates too slow to be of practical interest. Use of temperatures above this range causes excessive formation of undesired degradation products and requires operation in expensive high pressure equipment. The preferred temperature range is from about 205° C. to about 250° C. The reaction pressure is generally not a critical variable, except of course that it must be large enough to maintain the reactants in the liquid phase. Economic considerations almost always favor performing the process at the lowest possible pressure. Likewise, the molar ratio of contacted m-toluic acid and diethylamine is not a critical variable to the practice of this invention. Preferably, in order to avoid leaving wasteful amounts of either reactant unreacted, total quantities of m-toluic acid and diethylamine contacted are in a molar ratio of about 0.5:1 to 2:1.

The catalyzed liquid phase reaction described herein of m-toluic acid with diethylamine appears to be an equilibrium reaction. It is therefore highly desirable to remove the product water from the liquid reaction phase in order to force the reaction towards completion. One convenient method of removing water, which is common knowledge to those skilled in the art, comprises adding to the reaction mixture a small quantity of a volatile, water-immiscible, reaction-inert azeotroping agent for water, performing the preparation at reflux, collecting the condensed reaction vapors and allowing them to separate into an aqueous phase and an azeotropic agent phase (e.g., in a Dean-Stark trap), and then withdrawing the former and returning the latter to the reaction mixture. Excessive reflux and collection of diethylamine, which tends to render water miscible with most azeotropic agents used for water removal, is avoided by using a highly volatile azeotropic agent such as benzene or toluene. Water removal from the reaction mixture may also be effected by other methods known to the art such as by treatment of the mixture with molecular sieves during the course of the reaction.

The process of this invention may be operated as either a batch, continuous or semi-continuous process.

A preferred method of semi-continuous operation is described in the examples herein. When the latter procedure is employed, the full quantities of m-toluic acid and catalyst, but only a portion of the diethylamine, are charged to the reactor initially. The reaction mixture is refluxed while the remainder of the amine is fed to it. The rate of amine feed is adjusted to control the temperature of the reaction mixture. This mode of semi-continuous operation can be used of course in conjunction with the method of removing water by azeotropic distillation described above.

The starting materials, m-toluic acid and diethylamine, are readily available. Commercial grades of m-toluic acid manufactured by the oxidation of meta-xylene are often contaminated with impurities such as ortho-toluic acid, benzoic acid and, especially, iso-phthalic acid. These acids are converted to their respective di- or tetra (ethyl) amides but do not in any other way affect the novel process of this invention. Thus the high purity grade of m-toluic acid required for vapor phase catalytic reaction with secondary amine (see U.S. Pat. No. 2,932,665) is not required here.

The product N,N-di(ethyl)-meta-toluamide may be recovered from the liquid phase reaction mixture by conventional methods, such as by distillation under vacuum as is described in the examples herein.

Several important advantages are offered by the novel process described in this application. It involves only one chemical step which may be performed under a single set of reaction conditions. The cost of reactants other than m-toluic acid and diethylamine, e.g., phosphorus oxychloride, is eliminated. Meta-toluic acid is considerably more available and less expensive than meta-tolunitrile, the starting material in U.S. Pat. No. 3,825,596. The reaction products are the desired meta-toluamide and water. No equimolar quantities of reaction products such as ammonia or hydrogen chloride, which must be treated in order to avoid damage to the environment, are generated. Catalyst cost is low. The process is very well suited for commercial scale production. Other advantages are revealed elsewhere in the instant application.

This novel process may be conducted at reflux under about atmospheric pressure, using the preferred semi-continuous method described above with a reaction temperature of about 205° C. to 250° C., to produce the valuable product N,N-diethyl-meta-toluamide. Conversions of m-toluic acid to N,N-diethyl-meta-toluamide of as high as about 90 to 93% may be obtained.

The following examples illustrate the invention but are not to be construed as limiting the same.

EXAMPLE 1

Meta-toluic acid (544 g., 4.00 moles), diethylamine (73 g., 1.00 mole) and a mixture of Tyzor TE (4.0 g., E. I. du Pont de Nemours and Co., Inc., Wilmington, Del.) and benzene (ca. 15 ml.) were added to a flask fitted with a Dean-Stark trap (filled with benzene) and reflux condenser. The reaction mixture was heated without stirring to melt the meta-toluic acid (at ca. 107° C.), heated with stirring to reflux, and then stirred for about 22 hours at reflux under atmospheric pressure (ca. 220–235° C.). The lower (aqueous) layer was periodically withdrawn from the Dean-Stark trap in order to maintain a roughly constant amount of benzene in the reaction mixture. Additional diethylamine (274 g., 3.75 moles) was fed to the reaction mixture beneath the liquid surface during the first 18 hours of the reflux period at a rate adjusted to maintain the reaction temperature within the range cited above.

Potentiometric titration of the reaction mixture at the end of the reflux period showed 93% conversion of the starting meta-toluic acid.

The reaction mixture (696 g.) was then washed with 310 ml. of hot 25 weight percent aqueous sodium chloride solution containing ca. 1.1 moles per liter sodium hydroxide, washed with hot 26 weight percent aqueous sodium chloride solution (300 ml.), and then evaporated at 20–30 mm Hg to remove water, residual diethylamine and residual benzene. The reaction mixture weighed 612 g. at this point, with 56 g. of sampling and transfer losses having been realized since the start of the experiment. The reaction mixture was then distilled under nitrogen at 20 mm Hg to recover an N,N-diethyl-meta-toluamide distillate [550.5 g., >95 wt. % N,N-diethyl-meta-toluamide by refractive index (1.5215 at 25° C.) and specific gravity (0.9985 at 25° C.), ca. 75% yield, APHA color 25, 0.14 mmoles/kg. total acidity by potentiometric titration].

EXAMPLE 2

The procedure of Example 1 was followed except that titanium tetrachloride (1.6 g., added to the initial charge as a mixture with ca. 35 ml. benzene) was used as catalyst, and the starting meta-toluic acid contained a small amount of iso-phthalic acid. The reaction mixture was stirred for about 19 hours at reflux under atmospheric pressure (ca. 220–235° C.). Additional diethylamine (238 g., 3.25 moles) was fed during the first 18.5 hours of the reflux period.

Potentiometric titration of the reaction mixture at the end of the reflux period showed 93% conversion of meta-toluic acid. 562 grams N,N-diethyl-meta-toluamide distillate was recovered from the reaction mixtrue [97.1 wt. % N,N-diethylmeta-toluamide by gas-liquid chromatography (GLC), ca. 77% yield, 0.24 wt. % N,N,N',N'-tetraethyl-isophthalamide by GLC, APHA color 65, 1.97 mmoles/kg. total acidity by potentiometric titration].

EXAMPLE 3

The procedure of Example 1 was used except that titanium tetrachloride (4.0 g., added to the initial charge as a mixture with ca. 45 ml. benzene) was used as catalyst. The reaction mixture was stirred for about 22.5 hours at reflux under atmospheric pressure (ca. 225–240° C.). Additional diethylamine (238 g., 3.25 moles) was fed during the first 16 hours of the reflux period.

Potentiometric titration of the reaction mixture at the end of the reflux period showed 91% conversion of meta-toluic acid. 511 grams N,N-diethyl-meta-toluamide distillate was recovered from the reaction mixture [>95 wt. % N,N-diethylmeta-toluamide by GLC, ca. 68% yield, APHA color 25, 0.15 mmoles/kg. total acidity by potentiometric titration].

EXAMPLE 4

The procedure of Example 1 was used except that tetra(n-butyl) titanate (4.0 g., added to the initial charge as a mixture with ca. 20 ml. benzene) was used as catalyst. The reaction mixture was stirred for about 25.5 hours at reflux under atmospheric pressure (ca. 205–235° C.). Additional diethylamine (238 g., 3.25 moles) was fed during the first 25 hours of the reflux period.

Potentiometric titration of the reaction mixture at the end of the reflux period showed 93% conversion of meta-toluic acid. 563 grams N,N-diethyl-meta-toluamide distillate was recovered from the reaction mixture (ca. 74% yield, APHA color 45 — stable under 24 hrs. exposure to UV).

What is claimed is:

1. A process for the preparation of N,N-diethyl-meta-toluamide which comprises contacting meta-toluic acid with diethylamine in the liquid phase at a temperature of about 150° C. to 300° C. in the presence of a catalyst in the amount of about 0.0001 to 0.1 gram per gram of said meta-toluic acid, said catalyst being selected from the group consisting of titanium tetrachloride; $Ti(OA)_4$ wherein the four A moieties may be identical or not and each is selected from the group consisting of alkyl of from 3 to 18 carbon atoms; triethanolamine titanate chelates; titanium acetylacetonate chelates; tetraoctylene glycol titanate chelates; and titanium lactate ammonium salt chelates, and the water produced during said contacting being removed from said liquid phase during the course of said preparation.

2. The process of claim 1 wherein said catalyst is $Ti(OA)_4$ wherein A is as defined in claim 1.

3. The process of claim 2 wherein said catalyst is tetra(n-butyl) titanate.

4. The process of claim 1 wherein said catalyst is a triethanolamine titanate chelate.

5. The process of claim 1 wherein said catalyst is present in an amount of about 0.001 to 0.02 gram per gram of said meta-toluic acid.

6. The process of claim 1 wherein said temperature is about 205° C. to 250° C.

7. The process of claim 1 wherein meta-toluic acid and diethylamine are contacted in a molar ratio of about 0.5:1 to 2:1.

8. The process of claim 1 wherein said temperature is about 205° C. to 250° C., said preparation is performed at reflux under about atmospheric pressure, and said water is removed from said liquid phase by azeotropic distillation with benzene or toluene.

* * * * *